United States Patent
Turos et al.

(10) Patent No.: US 10,350,177 B2
(45) Date of Patent: Jul. 16, 2019

(54) ANTIBACTERIAL S-HETEROSUBSTITUTED DISULFIDES

(71) Applicants: Edward Turos, Wesley Chapel, FL (US); Praveen Ramaraju, Natchez, MS (US)

(72) Inventors: Edward Turos, Wesley Chapel, FL (US); Praveen Ramaraju, Natchez, MS (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/105,573

(22) Filed: Aug. 20, 2018

(65) Prior Publication Data

US 2018/0369163 A1    Dec. 27, 2018

Related U.S. Application Data

(63) Continuation of application No. 15/349,475, filed on Nov. 11, 2016, now Pat. No. 10,080,725, which is a continuation of application No. 12/765,272, filed on Apr. 22, 2010, now Pat. No. 9,512,160, which is a continuation of application No. PCT/US2008/081125, filed on Oct. 24, 2008.

(60) Provisional application No. 60/982,403, filed on Oct. 24, 2007.

(51) Int. Cl.
| | |
|---|---|
| *A61K 31/105* | (2006.01) |
| *C07C 321/14* | (2006.01) |
| *C07C 321/20* | (2006.01) |
| *A61K 31/145* | (2006.01) |
| *C07C 381/00* | (2006.01) |
| *C07H 15/00* | (2006.01) |

(52) U.S. Cl.
CPC .......... *A61K 31/105* (2013.01); *A61K 31/145* (2013.01); *C07C 321/14* (2013.01); *C07C 321/20* (2013.01); *C07C 381/00* (2013.01); *C07H 15/00* (2013.01); *C07C 2601/14* (2017.05)

(58) Field of Classification Search
CPC   A61K 31/105; A61K 31/145; C07C 2601/14; C07C 321/14; C07C 321/20; C07C 381/00; C07H 15/00
See application file for complete search history.

(56) References Cited

U.S. PATENT DOCUMENTS

2005/0148570 A1*  7/2005  Huang ................. A61K 31/075
                                                                514/192

OTHER PUBLICATIONS

Kim et. al., Food Science and Biotechnology, 2004, The Korean Society of Food Science and Technology, vol. 13(2), pp. 235-239 (Year: 2004).*

* cited by examiner

*Primary Examiner* — Sarah Pihonak
(74) *Attorney, Agent, or Firm* — Michele L. Lawson; Smith & Hopen, P.A.

(57) ABSTRACT

Synthetically-derived S,S-heterodisubstituted disulfides that exhibit potent in vitro antibacterial activity against a variety of bacteria, including *Staphylococcus aureus*, methicillin-resistant *Staphylococcus aureus* and *Francisella tularensis*. The present invention provides compounds, methods and compositions effective to treat microbial/bacterial infections, and, especially, infections arising from bacteria which have developed resistance to conventional antibiotics.

5 Claims, 2 Drawing Sheets

ANTIBACTERIAL S-HETEROSUBSTITUTED DISULFIDES

CROSS REFERENCE TO RELATED APPLICATIONS

This application is a continuation of and claims priority to currently pending U.S. Nonprovisional application Ser. No. 15/349,475, entitled "Antibacterial S-Heterosubstituted Disulfides", filed Nov. 11, 2016, which is a continuation of and claims priority to U.S. Nonprovisional application Ser. No. 12/765,272, entitled, "Antibacterial S-Heterosubstituted Disulfides", filed Apr. 22, 2010, now U.S. Pat. No. 9,512,160, which is a continuation of and claims priority to International Application Number PCT/US2008/081125, entitled, "Antibacterial S-Heterosubstituted Disulfides", filed Oct. 24, 2008, which claims priority to U.S. Provisional Patent Application No. 60/982,403 entitled, "Antibacterial S-Heterosubstituted Disulfides", filed Oct. 24, 2007, the contents of each of which are herein incorporated by reference.

STATEMENT OF GOVERNMENT INTEREST

This invention was made with government support under Grant No. R01 AI053281 awarded by the National Institutes of Health. The Government has certain rights in the invention.

FIELD OF INVENTION

This invention relates to antibiotic compositions. More specifically, this invention relates to antibacterial S-heterosubstituted disulfide compounds and methods of using these compounds.

BACKGROUND OF THE INVENTION

This invention addresses the severe need for new classes of antibacterial antibiotics for treatment of bacterial infections, and, especially infections arising from bacteria which have developed resistance to conventional antibiotics, such as methicillin-resistant infections of *Staphylococcus aureus* (MRSA), and bacterial species presenting significant health concerns due to their morbidity and mortality in epidemics, such as *Francisella tularensis* and *Bacillus anthracis*.

Antibiotic resistance is a particularly critical health concern and has increased dramatically over the past two decades. Antibiotic resistance refers to the ability of a microorganism to avoid the harmful effects of an antibiotic by destroying the antibiotic, transporting it out of the cell, or undergoing changes that block its effects. Frequent exposure of a microorganism to an antibiotic provides conditions favorable to the evolution of antibiotic resistance.

MRSA is a type of *Staphylococcus aureus* resistant to certain antibiotics including methicillin and the more common antibiotics such as oxacillin, penicillin, and amoxicillin. MRSA incidence is on the rise in the U.S. and it has now become recognized as a major community-acquired pathogen.

This invention addresses the severe need for new classes of antibacterial antibiotics for treatment of methicillin-resistant infections of *Staphylococcus aureus* (MRSA) which is of epidemic concern due to their lethality and difficulty in treating in hospitals and in the open community.

SUMMARY OF INVENTION

The present invention provides compounds, methods and compositions effective to treat bacterial infections, and, especially, infections arising from bacteria which have developed resistance to conventional antibiotics. These S-heterosubstituted disulfide compounds, synthetically-derived substances prepared in our laboratory, have novel chemical structures and potent in vitro antibacterial activity against MRSA. The mechanism of action of these compounds is thought to be similar, based on the structural and chemical similarities, to that of previously reported N-thiolated beta-lactams (N-alkylthio beta-lactams), which have been shown to create alkyl-CoA disulfides through a thiol-disulfide exchange within the cytoplasm ultimately inhibiting type II fatty acid synthesis. Given this mode of action in inhibiting fatty acid biosynthesis, the antibacterial activity of the compounds, as observed against *Francisella tularensis*, *Staphylococcus aureus* and methicillin-resistant *Staphylococcus aureus*, would extend to a wide cross-section of Gram-negative and Gram-positive bacteria, including *B. anthracis*, as well as serving as an antimicrobial against microbes such as fungi.

In accordance with the present invention there is provided a compound having the formula (I):

$$R_1X_1SSX_2R_2 \qquad (I)$$

Each of $X_1$ and $X_2$ of compound (I) can be O, N, NH, or S, with $X_1$ and $X_2$ not necessarily the same as one-another. For example, $X_1$ could be O, while $X_2$ is S. Additionally, each $R_1$ and $R_2$ are independently alkyl, alkenyl, alkynyl, aryl, heteroaryl, or heterocyclic. As with $X_1$ and $X_2$, $R_1$ and $R_2$ need not be the same. The compound can further comprise a pharmaceutically acceptable carrier.

In an advantageous embodiment, $X_1$ and $X_2$ are NH and $R_1$ and $R_2$ can be one of methyl, ethyl, propyl, isopropyl, butyl, s-butyl, or phenyl. In a particularly advantageous embodiment $R_1$ and $R_2$ are independently propyl or phenyl.

In a further advantageous embodiment of the first aspect of the invention, $X_1$ and $X_2$ are S and $R_1$ and $R_2$ can be one of methyl, ethyl, propyl, isopropyl, butyl, s-butyl, or phenyl. In a particularly advantageous embodiment at least one of $R_1$ and $R_2$ are phenyl.

In a still further advantageous embodiment of the first aspect of the invention, $X_1$ and $X_2$ are N and $R_1$ and $R_2$ can be one of dimethyl, diethyl, diisopropyl, diallyl, or diisobutyl. In a particularly advantageous embodiment at least one of $R_1$ and $R_2$ are dimethyl, or diallyl.

In a second aspect the present invention provides a compound having the formula (I):

$$R_1X_1SSX_2R_2 \qquad (I)$$

In the compound of the second aspect at least one of $X_1$ and $X_2$ is O and each $R_1$ and $R_2$ are independently alkyl, alkenyl, alkynyl, aryl, heteroaryl, or heterocyclic. If $X_1$ and $X_2$ are both O and $R_1$ and $R_2$ are both alkyl, then $R_1$ and $R_2$ are not both propyl, isopropyl or butyl. For example, if $R_1$ is propyl, then $R_2$ can be isopropyl or butyl, but not propyl.

In an advantageous embodiment, both $X_1$ and $X_2$ are O. $R_1$ and $R_2$ can independently be methyl, ethyl, propyl, isopropyl, butyl, s-butyl, or phenyl. In a particularly advantageous embodiment $R_1$ and $R_2$ are independently isopropyl, butyl, or phenyl.

In a third aspect the present invention provides a compound having the formula (I):

$$R_1X_1SSX_2R_2 \qquad (I)$$

In the compound of the third aspect each of $X_1$ and $X_2$ can independently be O, N, NH, or S and each $R_1$ and $R_2$ are independently alkyl, alkenyl, alkynyl, aryl, heteroaryl, or heterocyclic. However, if $X_1$ and $X_2$ are both O and $R_1$ and $R_2$ are both alkyl groups, then both of $R_1$ and $R_2$ are not propyl, isopropyl or butyl. In other words, they are not both the same alkyl group if one of $R_1$ and $R_2$ are propyl, isopropyl or butyl. For example, if $R_1$ is propyl, then $R_2$ can be isopropyl or butyl, but not propyl. The compound can further comprise a pharmaceutically acceptable carrier.

In a fourth aspect the present invention provides a composition comprising a pharmaceutically acceptable carrier and a compound having the formula (I):

$$R_1X_1SSX_2R_2 \qquad (I)$$

In the compound of the fourth aspect each of $X_1$ and $X_2$ can independently be O, N, NH, or S and each $R_1$ and $R_2$ are independently alkyl, alkenyl, alkynyl, aryl, heteroaryl, or heterocyclic.

In a fifth aspect the present invention provides a kit comprising an S-heterosubstituted disulfide and instructions for treating an infection. In an advantageous embodiment, the S-heterosubstituted disulfide can be any one of the compounds of the first four aspects above.

In a sixth aspect the present invention provides a method of treating or preventing a microbial infection, comprising administering to a subject in need thereof an effective amount of a compound comprising an S-heterosubstituted disulfide.

In an advantageous embodiment the method is practiced with an S-heterosubstituted disulfide having the formula (I):

$$R_1X_1SSX_2R_2 \qquad (I)$$

Each of $X_1$ and $X_2$ can independently be O, N, NH, or S and each $R_1$ and $R_2$ are independently alkyl, alkenyl, alkynyl, aryl, heteroaryl, or heterocyclic.

In a further advantageous embodiment of the sixth aspect of the invention the microbe is a bacterium. The bacterium can be a bacterium from a genus including *Staphylococcus, Bacillus, Francisella, Micrococcus, Streptococcus, Neisseria, Streptomyces,* and *Mycobacterium.* In a particularly advantageous embodiment the bacteria are methicillin-susceptible *Staphylococcus aureus,* methicillin-resistant *Staphylococcus aureus, Francisella tularensis* or *Bacillus anthracis.* Administering can be carried out by a route selected from the group consisting of oral, intravenous, and topical.

In a seventh aspect the present invention provides a method of treating or preventing a bacterial infection, by administering to a subject in need thereof an effective amount of a compound having the formula (I):

$$R_1X_1SSX_2R_2 \qquad (I)$$

Each of $X_1$ and $X_2$ can independently be O, N, NH, or S and each $R_1$ and $R_2$ are independently alkyl, alkenyl, alkynyl, aryl, heteroaryl, or heterocyclic.

In an advantageous embodiment of the seventh the bacterium is from the genus *Staphylococcus, Bacillus, Francisella, Micrococcus, Streptococcus, Neisseria, Streptomyces,* or *Mycobacterium.* In a particularly advantageous embodiment the bacteria are methicillin-susceptible *Staphylococcus aureus,* methicillin-resistant *Staphylococcus aureus, Francisella tularensis* or *Bacillus anthracis.* Administering can be carried out by a route selected from the group consisting of oral, intravenous, and topical.

In a seventh aspect the present invention provides a method of inhibiting the growth of *Francisella tularensis, Staphylococcus aureus* or methicillin-resistant *Staphylococcus aureus* by the step of contacting the *Francisella tularensis, Staphylococcus aureus* or methicillin-resistant *Staphylococcus aureus* with an effective amount of a compound comprising an S-heterosubstituted disulfide.

In an eighth aspect the present invention provides a method of inhibiting the growth of *Francisella tularensis, Staphylococcus aureus* or methicillin-resistant *Staphylococcus aureus* by the step of applying the S-heterosubstituted disulfide to a surface that may come into contact with the *Francisella tularensis, Staphylococcus aureus* or methicillin-resistant *Staphylococcus.*

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The present invention provides compounds, methods and compositions effective to treat bacterial infections, and, especially, infections arising from bacteria which have developed resistance to conventional antibiotics. These S-heterosubstituted disulfide compounds, synthetically-derived substances prepared in our laboratory, have novel chemical structures and potent in vitro antibacterial activity against MRSA. New antibacterial compounds are in urgent need, particularly those effective against MRSA. The S-heterosubstituted disulfides of the invention may represent a critical advance in the battle against infectious disease. It is therefore important to continue the development of these compounds, and to fully evaluate and exploit their potential as a new generation of anti-microbials. The compounds of the present invention (also referred to herein as S,S-Heterodisubstituted Disulfides and S-Heterosubstituted Disulfides) exhibit antibacterial activity against bacteria such as *Staphylococcus aureus,* methicillin-resistant *Staphylococcus aureus* and *Francisella tularensis.*

Figure 2:
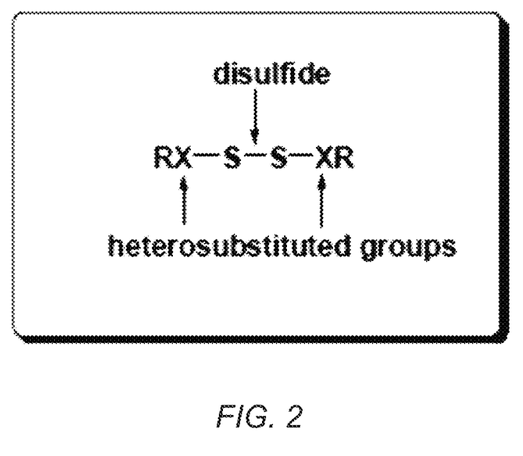
FIG. 2 is an illustration of the general formula for an S,S-Heterodisubstituted Disulfide ("S-Heterosubstituted Disulfide").

The present invention provides compounds having the general formula:

$$R_1X_1SSX_2R_2 \qquad (1)$$

or alternatively represented as:

$$(2)$$

$$\text{disulfide} \downarrow$$
$$R_1X_1 - S - S - X_2R_2$$
$$\uparrow \qquad \uparrow$$
$$\text{heterosubstituted groups}$$

where X can be O, N, NH, or S (in any combination), and R can include the groups of alkyl, alkenyl, alkynyl, aryl, heteroaryl, heterocyclic (such as a beta-lactam or 2-oxazolidinone), and so on, as is presented more fully below. The compounds may or may not be symmetrical in their substitution, so by way of example, $CH_3O-S-S-OCH_3$ could be one version of a symmetrical compound, while additional compounds can be of the form $CH_3O$—S—S—$OCH_2CH_3$ or $CH_3O$—S—S—$NHCH_3$, thus adopting asymmetric heterosubstituted groups.

The evidence indicates that the compounds block bacterial growth and replication by inhibiting fatty acid biosynthesis in the microorganism, though the details of the mode of action remains to be fully elucidated. The compounds of the present invention may therefore be used to prevent, alleviate, or cure diseases caused by pathogens whose growth is inhibited by these compounds. The instant compounds are particularly active against bacteria and bacteria-like microorganisms. They are therefore proposed for use in human and veterinary medicine, for the prophylaxis and chemotherapy of local and systemic infections caused by these pathogens. As used herein, the terms "treat", "treating", and "treatment" include therapy that alleviates one or more symptoms caused by the infection, or that cures the underlying infection. As used herein, the terms "prevent", "preventing", and "prevention" include prophylaxis, complete prevention, or delaying onset of the infection or delaying onset of one or more symptoms caused by the infection. Optionally, the method further comprises identifying the human or non-human subject as one suffering from a specific or non-specific bacterial infection. The presence of a bacterial infection can be determined using methods known to those of ordinary skill in the art of clinical diagnosis of disease (e.g., infectious disease).

The invention further encompasses methods for inhibiting the growth of bacteria by contacting the bacteria with an effective amount of the compounds of the invention in vitro or in vivo, or by applying the compound to a substrate (surface) likely to come in contact with the bacteria, such as a work surface, table, surgical instrument, implant or other device to be placed in or on the body (i.e., foreign object to be inserted into a subject, such as a stent, catheter, access port, intravenous delivery tube, heart valve, dental implant, electro-mechanical device, prosthetic device, glucose sensor, or stabilizing device such as orthopedic nails and pins), eating or cooking utensil, etc. Because of their powerful antibacterial properties, the present compounds may also be used to supplement feed for animals.

In addition, the compounds of the present invention that exhibit antibacterial activity may also be used as medicaments, and also as substances for preserving inorganic and organic materials, especially organic materials of all kinds, for example, polymers, lubricants, paints, fibers, leather, paper, timber, foodstuffs, and water. For example, these compounds can be covalently bonded to the polymer.

Definitions

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents, "administration" and its variants are each understood to include concurrent and sequential introduction of the compound or prodrug thereof and other agents.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to a microbial infection, an effective amount comprises an amount sufficient to kill or inhibit the growth and replication of the microbe. In some embodiments, an effective amount is an amount sufficient to delay development. In some embodiments, an effective amount is an amount sufficient to prevent or delay occurrence and/or recurrence. An effective amount can be administered in one or more doses.

As used herein, "treatment" refers to obtaining beneficial or desired clinical results. Beneficial or desired clinical results include, but are not limited to, any one or more of: alleviation of one or more symptoms, diminishment of extent of infection, stabilization (i.e., not worsening) of the state of infection, preventing or delaying spread of the disease (such as pathogen growth or replication), preventing or delaying occurrence or recurrence of the disease, delay or slowing of disease progression and amelioration of the disease state. The methods of the invention contemplate any one or more of these aspects of treatment.

A "subject in need of treatment" is a mammal with a microbial infection that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

A "pharmaceutically acceptable carrier" is a carrier, such as a solvent, suspending agent or vehicle, for delivering the compound or compounds in question to the animal or human. The carrier may be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The compounds of the present invention include all hydrates and salts of the S-heterosubstituted disulfides that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts. When reference is made to a compound or administering a compound, the recitation of the compound includes the a pharmaceutically acceptable salt thereof.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium or lithium) or alkaline earth metal (for example calcium) salts of carboxylic acids can also be made.

The compounds of the present invention can be formulated as pharmaceutical compositions and administered to a patient, such as a human patient, in a variety of forms adapted to the chosen route of administration, e.g., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient presenting the previously sterile-filtered solutions.

For topical administration, the present compounds may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from adsorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art (U.S. Pat. No. 4,938,949 (Borch et al.)).

Accordingly, the invention includes a pharmaceutical composition comprising a compound of the present invention as described above, or a pharmaceutically acceptable salt thereof, in combination with a pharmaceutically acceptable carrier. Pharmaceutical compositions adapted for oral, topical or parenteral administration, comprising an amount of one or more compounds effective to treat a bacterial infection, are a preferred embodiment of the invention.

The following definitions are used, unless otherwise described. Halo is fluoro, chloro, bromo, or iodo. "Alkyl," "alkoxy," etc. denote both straight and branched groups, but reference to an individual radical such as "propyl" embraces only the straight chain radical, a branched chain isomer such as "isopropyl" being specifically referred to. "Aryl" denotes a phenyl radical or an ortho-fused bicyclic carbocyclic radical having about nine to ten ring atoms in which at least one ring is aromatic. "Heteroaryl" encompasses a radical attached via a ring carbon of a monocyclic aromatic ring containing five or six ring atoms consisting of carbon and one to four heteroatoms each selected from the group consisting of non-peroxide oxygen, sulfur, and $N(R_x)$ wherein $R_x$ is absent or is hydrogen, oxo, alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. "Heteroalkyl" encompasses the replacement of a carbon atom within an alkyl chain with a heteroatom; e.g., replacement with an element other than carbon such as N, S, or O, including both an alkyl interrupted by a heteroatom as well as an alkyl substituted by a heteroatom.

It will be appreciated by those skilled in the art that compounds of the invention having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase), and how to determine antibacterial activity using the tests described herein, or using other tests which are well known in the art. Specific and preferred values listed below for radicals, substituents, and ranges, are for illustration only; they do not exclude other defined values or other values within defined ranges for the radicals and substituents.

Specifically, unless otherwise indicated, "alkyl" can include, for example, methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; "alkenyl" can include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradecenyl, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl; "alkoxy" can include methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy; "alkanoyl" can include acetyl, propanoyl, butanoyl, pentanoyl, hexanoyl, heptanoyl, octanoyl, nonanoyl, decanoyl, undecanoyl, dodecanoyl, tridecanoyl, tetradecanoyl, or pentadecanoyl; "cycloalkyl" can include cyclopropyl, cyclobutyl, cyclopentyl, cyclohexyl, cycloheptyl, or cyclooctyl. "Aryl" can include phenyl, indenyl, 5,6,7,8-tetrahydronaphthyl, or naphthyl. "Heteroaryl" can include furyl, imidazolyl, tetrazolyl, pyridyl, (or its N-oxide), thienyl, pyrimidinyl (or its N-oxide), indolyl, or quinolyl (or its N-oxide). "Heterocyclic" can include beta-lactam or 2-oxazolidinone.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state. Preferably, the compound of the invention (S-heterosubstituted disulfides) is administered in an isolated or pure form.

As used in this specification, the singular forms "a", "an", and "the" include plural reference unless the context clearly dictates otherwise. Thus, for example, a reference to "a microorganism" includes more than one such microorganism. A reference to "a cell" includes more than one such cell, and so forth. A reference to "a compound" includes more than one such compound.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. Eds. (1991) IRL Press)), each of which are incorporated herein by reference in their entirety.

This invention addresses the severe need for new classes of antibacterial antibiotics for treatment of bacterial infections, and, especially infections arising from bacteria which have developed resistance to conventional antibiotics, such as methicillin-resistant infections of *Staphylococcus aureus* (MRSA), and bacterial species presenting significant health concerns due to their lethality in epidemics, such as *Francisella tularensis* and *Bacillus anthracis*. The invention is now further described by way of the following examples, which, while illustrative of the invention, are not intended as limitations to the scope. It should be understood that the examples and embodiments described herein are for illustrative purposes only and that various modifications or changes in light thereof will be suggested to persons skilled in the art and are to be included within the spirit and purview of this application.

Example 1—Synthesis and Antibacterial Activity of S-Heterosubstituted Disulfides The target heterosubstituted disulfides are prepared by thiolation according to the following reaction:

(X = O, N, or S)

Representative synthesized compounds are presented in Table 1.

Figure 1:
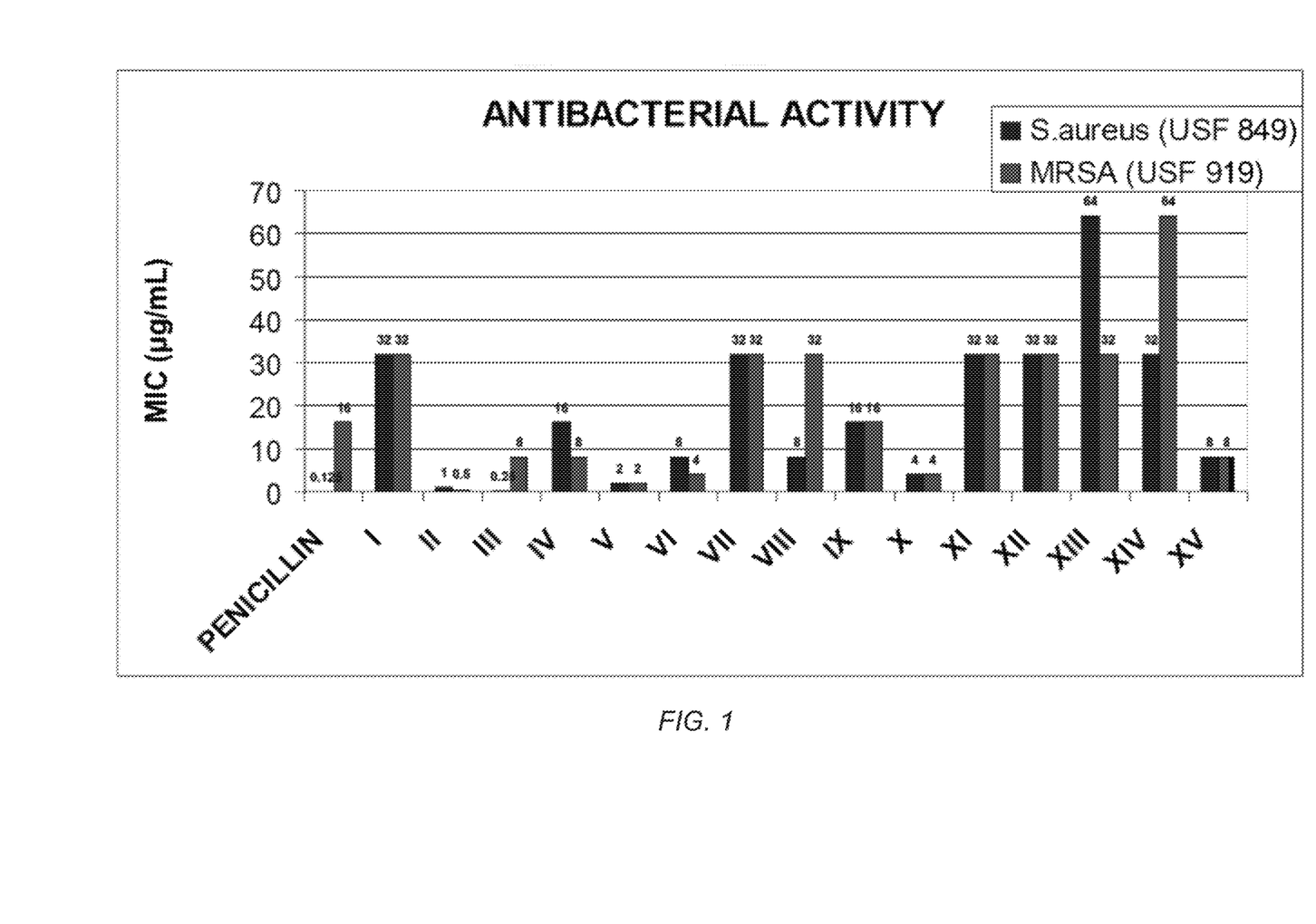
FIG. 1 is a bar graph illustrating the bioactivity of compounds I-XV and penicillin against *Staphylococcus aureus* and methicillin-resistant *Staphylococcus aureus.* Bioactivity was tested by agar dilution assay.

Bioactivity was tested by agar dilution assay against *Staphylococcus aureus* and methicillin resistant *Staphylococcus aureus* (Table 2). The compounds of the invention were evaluated against *Staphylococcus aureus* and methicillin-resistant *Staphylococcus aureus* bacteria strains (i.e. strains ATCC-849 and ATCC-919, respectively) by determining the minimum inhibitory concentration (MIC, µg/ml) of each compound with respect to each strain. The MIC, or minimum inhibitory concentration, is the lowest concentration of antibiotic which inhibits growth of the test organism and was determined for the synthesized compounds by the agar dilution method. A control plate with a reference drug, penicillin G, was used as the control.

As can be seen in the table, many of the synthesized compounds were as effective, or more effective, against MRSA than the Penicillin G control, even if they were not as effective as the control against *Staphylococcus aureus*.

While not intending to be bound to a particular theory, the mechanism of action of these compounds is thought to be similar, based on the structural and chemical similarities, to that of previously reported N-thiolated beta-lactams (N-alkylthio beta-lactams), which have been shown to create alkyl-CoA disulfides through a thiol-disulfide exchange within the cytoplasm ultimately inhibiting type II fatty acid synthesis. These compounds may also be characterized as essentially "stable" analogues of natural disulfides obtained from garlic and onions, which are fatty acid biosynthesis inhibitors. Given this mode of action in inhibiting fatty acid biosynthesis, the antibacterial activity of the compounds, as observed against *Francisella tularensis*, *

TABLE 1-continued

Antibacterial S-Hetero Substituted Disulfides

XIV: sec-butyl-S-S-S-S-sec-butyl tetrasulfide

XV: phenyl-S-S-S-S-phenyl tetrasulfide

XVI: (CH₃)₂N—S—S—N(CH₃)₂

XVII: (Et)₂N—S—S—N(Et)₂

XVIII: (iPr)₂N—S—S—N(iPr)₂

XIX: (allyl)₂N—S—S—N(allyl)₂

XX: (iBu)₂N—S—S—N(iBu)₂

TABLE 2

Anti-*Staphylococcus aureus* Activity Data

| | | | MIC (µg/mL) | |
|---|---|---|---|---|
| Substrate | Compound | R | S.A.[1] | MRSA[2] |
| Alcohol | I | propyl | 32 | 32 |
| | II | isopropyl | 1 | 0.5 |
| | III | butyl | 0.25 | 8 |
| | IV | s-butyl | 16 | 8 |
| | V | phenyl | 2 | 2 |
| 1° Amine | VI | propyl | 8 | 4 |
| | VII | isopropyl | 32 | 32 |
| | VIII | butyl | 8 | 32 |
| | IX | s-butyl | 16 | 16 |
| | X | phenyl | 4 | 4 |
| Thiol | XI | propyl | 32 | 32 |

TABLE 2-continued

Anti-*Staphylococcus aureus* Activity Data

| | | | MIC (µg/mL) | |
|---|---|---|---|---|
| Substrate | Compound | R | S.A.[1] | MRSA[2] |
| | XII | isopropyl | 32 | 32 |
| | XIII | butyl | 64 | 32 |
| | XIV | s-butyl | 32 | 64 |
| | XV | phenyl | 8 | 8 |
| 2° Amine | XVI | dimethyl | 0.25 | 0.5 |
| | XVII | diethyl | 2 | 2 |
| | XVIII | diisopropyl | 2 | 1 |
| | XIX | diallyl | 1 | 0.5 |
| | XX | diisobutyl | 16 | 16 |
| Control | Penicillin G | | 0.125 | 16 |

[1]S.A: *Staphylococcus aureus* (ATCC-849)
[2]MRSA: Methicillin Resistant *Staphylococcus aureus* (ATCC-919)

TABLE 3

Anti-tularaemia Activity Data

| Substrate | Compound | R | MIC (µg/mL)* |
|---|---|---|---|
| Alcohol | I | propyl | 16 |
| | II | isopropyl | 4 |
| | III | butyl | 4 |
| | IV | s-butyl | 16 |
| | V | phenyl | 1 |
| 1° Amine | VI | propyl | 16 |
| | VII | isopropyl | 2 |
| | VIII | butyl | 4 |
| | IX | s-butyl | 8 |
| | X | phenyl | 0.5 |
| Thiol | XI | propyl | 1 |
| | XII | isopropyl | 8 |
| | XIII | butyl | 4 |
| | XIV | s-butyl | 16 |
| | XV | phenyl | 2 |
| 2° Amine | XVI | dimethyl | 8 |
| | XVII | diethyl | 16 |
| | XVIII | diisopropyl | 32 |
| | XIX | diallyl | 16 |
| | XX | diisobutyl | 1 |
| Control | Ciprofloxacin | | 16 |

*MIC values against Live Vaccine Strain of *Francisella tularensis* using broth dilution technique.

TABLE 4

Antibacterial S-Hetero Substituted Disulfides

I: propyl-O-S-S-O

TABLE 4-continued

Antibacterial S-Hetero Substituted Disulfides

| Structure | No. |
|---|---|
| PhO-S-S-OPh | V |
| PrNH-S-S-NHPr | VI |
| iPrNH-S-S-NHiPr | VII |
| BuNH-S-S-NHBu | VIII |
| sec-BuNH-S-S-NH-sec-Bu | IX |
| PhNH-S-S-NHPh | X |
| Pr-S-S-S-S-Pr | XI |
| iPr-S-S-S-S-iPr | XII |
| Bu-S-S-S-S-Bu | XIII |
| sec-Bu-S-S-S-S-sec-Bu | XIV |
| PhS-S-S-SPh | XV |
| Me$_2$N-S-S-NMe$_2$ | XVI |
| Et$_2$N-S-S-NEt$_2$ | XVII |
| (iPr)(Et)N-S-S-N(iPr)(Et) | XVIII |
| (allyl)$_2$N-S-S-N(allyl)$_2$ | XIX |
| (iBu)$_2$N-S-S-N(iBu)$_2$ | XX |
| sec-BuO-S-S-O-sec-Bu (R,R) | XXI |
| sec-BuO-S-S-O-sec-Bu (S,S) | XXII |
| PhCH(Et)O-S-S-OCH(Et)Ph | XXIII |
| PhCH(Me)CH$_2$O-S-S-OCH$_2$CH(Me)Ph | XXIV |

TABLE 4-continued

Antibacterial S-Hetero Substituted Disulfides

XXV

XXVI

XXVII

XXVIII

TABLE 4-continued

Antibacterial S-Hetero Substituted Disulfides

XXIX

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for treating or preventing a bacterial infection, comprising administering to a subject in need thereof an effective amount of a compound comprising an S-heterosubstituted disulfide having formula (I):

$$X_1SSX_2 \qquad (I)$$

wherein each $X_1$ and $X_2$ are concurrently S—$R_1$;
wherein $R_1$ is phenyl.

2. The method of claim 1, further comprising a pharmaceutically acceptable carrier.

3. The method of claim 1, wherein the bacteria is *Staphylococcus aureus*.

4. The method of claim 3, wherein the bacteria is methicillin-resistant *Staphylococcus aureus*.

5. The method of claim 1, wherein the bacteria is *Francisella tularensis*.

\* \* \* \* \*